United States Patent [19]

Lollar

[11] Patent Number: 5,156,161

[45] Date of Patent: Oct. 20, 1992

[54] SKINFOLD CALIPER FOR BODY FAT MEASUREMENT

[76] Inventor: John A. Lollar, 19630 Victorian Dr., #11, Parker, Colo. 80134

[21] Appl. No.: 739,869

[22] Filed: Aug. 2, 1991

[51] Int. Cl.$^5$ .............................................. A61B 5/103
[52] U.S. Cl. .................................. 128/774; 606/205; 33/512
[58] Field of Search ............... 128/774; 606/205, 206, 606/210; 33/511, 512

[56] References Cited

U.S. PATENT DOCUMENTS

| | | | |
|---|---|---|---|
| 2,215,884 | 9/1940 | Runge | 33/512 |
| 2,619,956 | 12/1952 | Torricelli | 33/512 |
| 3,140,546 | 7/1964 | Bartlett | 33/148 |
| 3,140,715 | 7/1964 | Whitton et al. | 606/210 |
| 3,478,435 | 11/1969 | Cook | 33/511 |
| 3,906,957 | 9/1975 | Weston | 128/321 |
| 3,921,640 | 11/1975 | Freeborn | 128/318 |
| 4,127,112 | 11/1978 | Sherlock et al. | 128/2 S |
| 4,233,743 | 11/1980 | Flick | 33/143 |
| 4,312,363 | 1/1982 | Rothfuss et al. | 128/774 |
| 5,047,046 | 9/1991 | Bodoia | 606/205 |

Primary Examiner—Max Hindenburg
Attorney, Agent, or Firm—Dorr, Carson, Sloan & Petersen

[57] ABSTRACT

A skinfold caliper for measuring body fat percentages having two opposing clamping surfaces mounted on rigid arms which are connected at their lower end by a resilient member. The caliper includes a cantilever arm having a substantially circular projection engaging a dimple formed in the caliper when the clamping surfaces exert a predetermined pressure level. This creates an audible and tactile signal to the person performing the measurement indicating that the predetermined pressure level has been reached. A slide on a measuring scale is engaged by one of the arms as the clamping surfaces move toward one another and releases the slide as the clamping surfaces move away from one another. The pointer on the slide will thus stay at the point on the scale where the clamping surfaces gauged the thickness of the subcutaneous layer of fat of the skinfold.

17 Claims, 2 Drawing Sheets

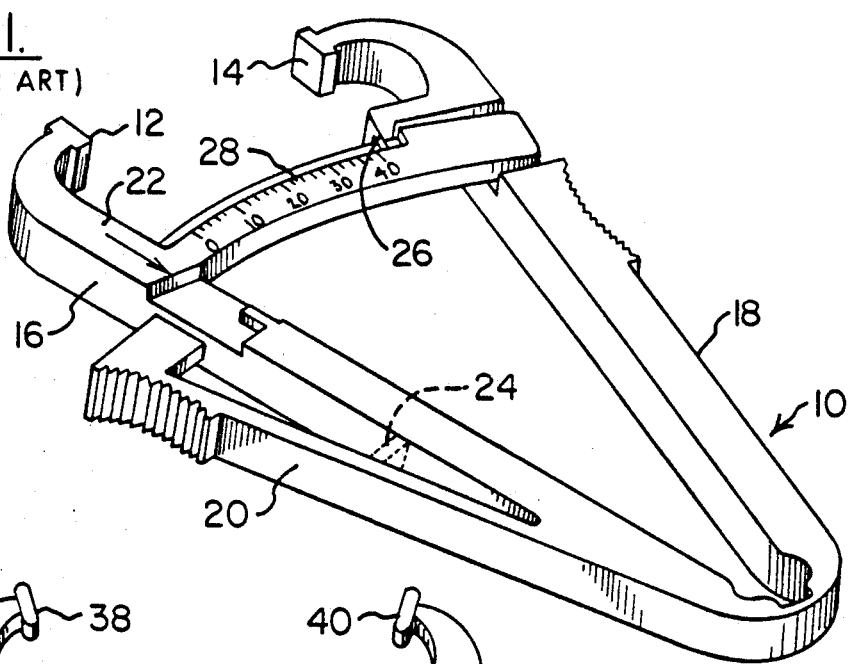
FIG. 1. (PRIOR ART)
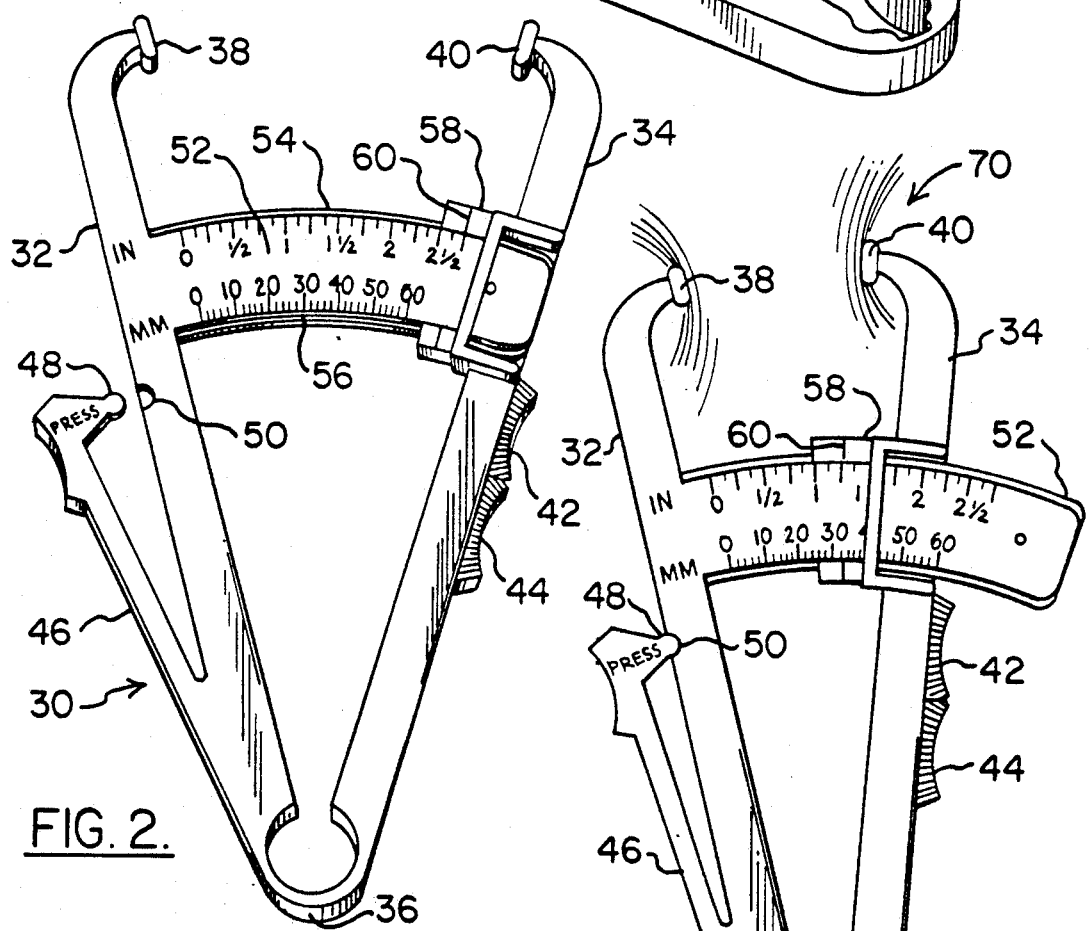
FIG. 2.
FIG. 3.

SKINFOLD CALIPER FOR BODY FAT MEASUREMENT

BACKGROUND OF THE INVENTION

1. Field of the Invention

The present invention relates to the field of body fat measurement, and particularly to the use of skinfold calipers for self-measurement of body fat.

2. Statement of the Problem

Presently, there is great emphasis based on personal health, fitness, and weight control. Many people, not just athletes, are concerned with these issues. One relevant index of weight and fitness is body fat percentage. However, present procedures for testing body fat percentages leave much to be desired in terms of practicality and convenience for most people.

Many procedures for testing body fat percentages are expensive and require elaborate equipment and procedures. These typically include underwater weighing, ultrasound, electrical impedance, and other procedures. These are normally limited to use in hospitals, clinics, health clubs and the like due to their expense and complexity.

One alternative procedure to these elaborate methods of testing body fat percentage is the measurement of body fat percentage by a skinfold caliper. Skinfold measurements are taken by pinching the skin and the flexible subcutaneous layer of the fat below the skin at selected positions on the body. These measurements are referenced to a table to determine the relative percentage of fat. One concern with these measurements is the accurate reading of the measurements and also the applied pressure of the caliper jaws during the measurement, since the skin and subcutaneous layer of fat is somewhat resilient. Typically, these skinfold calipers are also quite expensive and limited to the medical industry. Normally, these skinfold calipers require the aid of medical personnel or other trained personnel to administer the procedure measurement.

One such caliper of this type is disclosed in U.S. Pat. No. 3,008,239, issued to Lange. This caliper applies a constant pressure during the measurement by the use of a helical spring. However, this device is relatively complex, using levers and gears to achieve a "constant" spring force and the accuracy of the device deteriorates with the loss of the spring force. Also the measurement must be read by others in order to get an accurate reading.

Similarly, U.S. Pat. No. 4,233,743, issued to Flick, discloses a spring-loaded skinfold caliper. This caliper uses two jaws which are linearly movable relative to one another and resiliently biased together. The spring applies constant pressure on the skinfold. This device is relatively complex and normally requires another person to accurately read the measurement.

U.S. Pat. No. 3,140,543, issued to Bartlett, discloses a skinfold caliper having two opposing lever arms with a measuring scale extending from one of the arms. A helical spring biases the arms together. This type of caliper uses the spring to apply "constant" pressure during the measurement. However, the spring force may deteriorate during use and may become non-linear. Also the pointer on the measuring scale must be read during the measurement, requiring another person in order to obtain an accurate measurement.

U.S. Pat. No. 4,312,363, issued to Rothfuss et al. discloses a caliper for measuring tissue thickness for surgical purposes. This caliper uses a spring to exert a pressure on two opposing jaws and a scale and pointer type measuring scale.

U.S. Pat. No. 3,921,640, issued to Freeborn, and U.S. Pat. No. 3,906,957, issued to Weston, both disclose surgical devices using spring biased opposing jaws. Neither of these devices are able to accurately determine body fat percentage by self-measurement.

A one-piece, plastic skinfold caliper is disclosed in U.S. Pat. No. 4,127,112, issued to Sherlock et al. This caliper uses two opposing arms connected by a spring arm with a measuring scale formed on one arm and a pointer on the other arm. Jaws are formed on the free end of each arm opposing one another. The arms are clamped over the skin fold until a predetermined force is reached as indicated by a flag on a spring-like member. The measurement is then read visually directly by the alignment of the pointer on the scale. This skinfold caliper is difficult to use without the use of an another person to align the flag to determine the force and to read the skin fold measurement on the measuring scale.

Therefore a need exists for an inexpensive skinfold caliper that is usable by a single individual to accurately measure his/her own body fat percentage.

3. Solution to the Problem

The present invention solves these problems and others by providing a skinfold caliper for an individual to self measure body fat percentage.

The present invention provides a skinfold caliper that indicates when the appropriate pressure level has been applied.

The present invention provides a skinfold caliper that can be operated by a single individual without the need for additional personnel.

The present invention provides a skinfold caliper that retains the measurement so the individual can accurately read the measurement.

The present invention provides a skinfold caliper that is relatively inexpensive.

These and other features will be evident from the ensuing description of the invention and from the drawings.

SUMMARY OF THE INVENTION

The present invention provides a skinfold caliper for self-measurement of body fat percentage. The skinfold caliper of the present invention enables a person to self-measure their bodyfat percentage with complete privacy. The skinfold caliper of the present invention includes two opposing clamping surfaces mounted on rigid arms which are connected at their lower end by a resilient member. The opposing clamping surfaces are thus pivotally mounted about a fixed radius on a common pivot point. A cantilever arm is affixed to one of the arms. The cantilever arm has a inwardly directed substantially circular projection extending towards the arm. A dimple is formed in the arm opposing the projection for engagement with the projection. The dimple includes a neck portion for resiliently resisting engagement with the projection until a predetermined force is exerted by the opposing clamping surfaces clamping the resilient subcutaneous layer of fat of a skinfold. This force is predetermined so that approximately ten grams per square millimeter ($10 \text{ g/mm}^2$) of pressure is exerted against the layer of fat. This pressure is the standard used for measuring body fat percentage.

The engagement of the projection in the dimple indicates that this pressure level has been reached. This signals the person doing the measurement by tactually sensing the "click" of the projection moving past the neck portion of the dimple and by the audible "click". Thus, the person doing the measurement is not forced to visually align indicator lines as in prior art devices.

A measuring scale extends inwardly from one of the arms with inch and/or millimeter scales formed thereon. A slide having at least one pointer line is slidably mounted on the scale. The opposing arm includes a surface which engages the slide when the clamping surfaces move toward one another and releases the slide when the clamping surfaces move away from one another. The pointers on the slide will thus stay at the point on the scale where the clamping surfaces gauged the thickness of the subcutaneous layer of fat of the skinfold.

In operation, the person performing the measurement on themselves "pinches" a skinfold at a selected body site. The subcutaneous layer of fat is pulled away from the underlying muscle tissue at this site. The skinfold is engaged by the clamping surfaces of the caliper by compressing the arms toward one another. Once the person doing the measuring feels the "click" of the projection in the dimple or hears the "click", the caliper is released to allow the arms to spring open to unclamp the skinfold. The pointers on the slide remain at the gauged thickness. The measured thickness can then be determined from the scale. This measurement is applied to a chart, table, slide rule or the like to determine the body fat percentage of the person performing the measurement.

Other embodiments include the use of an electronic sensor to monitor the stress of the caliper to determine the predetermined pressure level from the clamping surfaces which then emits an audible signal. The present invention encompasses other variations and modifications within the scope of the inventive concept. These and other features of the present invention will become evident from the ensuing description of a preferred embodiment in conjunction with the drawings.

BRIEF DESCRIPTION OF THE DRAWINGS

FIG. 1 is a perspective of a prior art device.

FIG. 2 is a front perspective of a preferred possible embodiment of the present invention.

FIG. 3 is a front view of the embodiment of FIG. 2 measuring a skinfold.

DETAILED DESCRIPTION OF A PREFERRED EMBODIMENT

Figure 4:
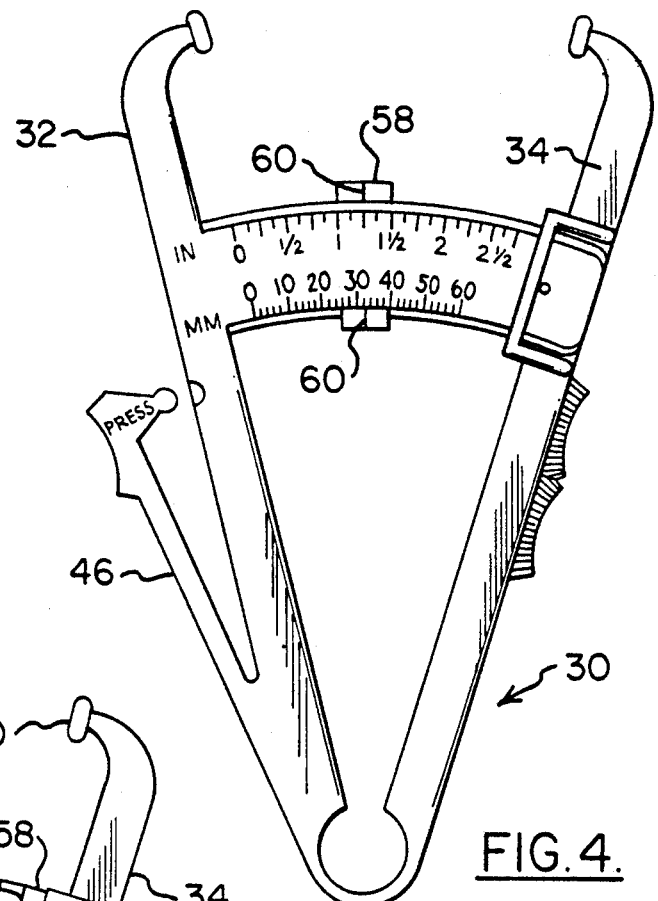
FIG. 4 is a front view of the embodiment of FIG. 2 after a measurement.

The present invention provides a skinfold caliper for self-measurement of the thickness of a subcutaneous layer of fat to obtain the body fat percentage of a person. A typical prior art skinfold caliper 10 is illustrated in FIG. 1. This type of caliper is used by grasping a skinfold of a person by the opposing clamping surfaces 12, 14 formed on rigid arms 16, 18 which are connected by a spring portion. The subcutaneous layer of fat is pulled away from the underlying muscle tissue. The opposing surfaces 12, 14 are clamped at a predetermined pressure level, normally ten grams per square millimeter (10 gm/mm$^2$), in order to overcome the resilience of the subcutaneous fat layer. This pressure level is indicated by the alignment of resilient arm 20 with arrow 22. If necessary, a stiffener 24 is used to provide further resistance against the resilient arm 20. The thickness of the resilient subcutaneous fat layer is measured by pointer 26 aligned on measuring scale 28. This measurement is then applied to a chart, slide rule or computer to determine the body fat percentage of the individual.

This type of caliper requires the assistance of other people in order to obtain an accurate measurement. It is difficult to align resilient arm 20 with arrow 22 and to read the measurement off scale 28 aligned with pointer 26 without another person performing the measurement present. Also, accurate readings are difficult to obtain since the alignment and measurement must occur simultaneously.

The present invention provides a skinfold caliper that can be operated by the person being measured without the need for assistance from other people. Also, it is relatively easy to obtain accurate readings with the device of the present invention.

One possible preferred embodiment is illustrated in FIGS. 2-4. It is to be expressly understood that the present invention is not to be limited to this descriptive embodiment. The preferred embodiment is meant for explanatory purposes only and is not meant to limit the scope of the claimed inventive concept. Other embodiments and modifications are considered to be within the scope of the claimed invention.

Skinfold caliper 30, shown in FIG. 2, includes two opposing clamping surfaces 38, 40 formed on the upper ends of elongated rigid arms 32, 34. Arms 32, 34 are joined on the lower ends by resilient member 36. Clamping surfaces 38, 40 are thus movable relative to one another through a fixed radius about a common pivot point. Arms 32, 34 and clamping surfaces 38, 40 are biased away from each other by resilient member 36. The skinfold of a person being measured is manually compressed by clamping surfaces 38, 40 by the applying pressure on raised concave grip surfaces 42 and thumb grip surface 44.

Thumb grip surface 44 is formed on cantilever arm 46 extending substantially parallel to arm 32 and affixed to the lower end portion of arm 32. Substantially circular projection 48 extends perpendicularly from cantilever arm 46 inward towards arm 32. Dimple 50 is formed in arm 32 for engagement with projection 48 on cantilever arm 46 as clamping surfaces 38, 40 are moved toward one another by compression of grips surface 42 and thumb grip surface 44. Dimple 50 includes a resilient neck portion having an opening slightly less than the diameter of projection 38 to provide resilient resistance to the projection 38 engaging dimple 50. This resistance is designed to be overcome as clamping surfaces 38, 40 engage the resilient subcutaneous layer of fat at a pressure of approximately ten grams per square millimeter (10 gm/mm$^2$) This pressure level is the standard normally used in body fat percentage measurements.

As projection 48 overcomes the resilient resistance from the neck portion of dimple 50 to fully engage in dimple 50, the person compressing caliper 30 is able to tactually sense the engagement as an indication that clamping surfaces 38, 40 are at a pressure level of approximately ten grams per square millimeter (10 gm/mm$^2$) without the need to visually inspect the caliper. Also, this engagement of projection 48 into dimple 50 emits an audible "click". The audible "click" will also serve as an indication of the appropriate pressure level.

Measuring scale 52 extends substantially perpendicular from arm 32 inward towards arm 34. Scale 52 has an arcuate shape at approximately the same arc as the arc of the pivoting motion of arms 38, 40. Upper edge 54 of scale 52 has an inch scale imprinted thereon and lower edge 56 of scale 52 has a millimeter scale imprint.

Slide 58 is mounted on scale 52 for movement relative to scale 52. Slide 58 engages in a recess on upper edge 54 and a recess on lower edge 56 to be flush with the surface o of scale 52. Line 60 formed from each edge on the surface of slide 58 provides pointers or indicators to measure the gauged thickness of the layer being measured from the respective scales.

Scale 52 engages in raised support 62 on arm 34 and is movable relative to support 62. Engaging surface 64 engages slide 58 as clamping surfaces 38, 40 move toward one another and releases slide 52 as clamping surfaces 38, 40 move away from one another. This allows slide 58 to remain at the measured position after the caliper is released.

In operation, as shown in FIGS. 3 and 4, a skinfold is measured by caliper 30 by pulling skinfold 70 and the underlying layer of fat away from the muscle tissue. Clamping surfaces 38, 40 are compressed over skinfold 70 by gripping surfaces 42, 44 in one hand and squeezing arms 32, 34 together. Engaging surface 64 moves slide 58 across scale 52 as clamping surfaces 38, 40 compress skinfold 70 and the resilient layer of fat. Once clamping surfaces 38, 40 reach the predetermined pressure level (ten grams per square millimeter), projection 48 will overcome the resilient neck portion of dimple 50 and fully engage in dimple 50. This engagement will be felt by the person doing the measurement as well as heard, as the projection will actually emit an audible "click". This will indicate to the person that the measurement has reached the appropriate pressure level. Arms 32, 34 are released and clamping surfaces 38, 40 are removed from skinfold 70.

Engaging surface 64 will release slide 58 as arms 32, 34 move apart so that slide 58 will remain in place, as shown in FIG. 4. The gauged thickness of the fat layer can now be measured by the position of pointers 60 on scale 52. The measurement can be obtained in either inches or millimeters. This measurement can be applied to a corresponding chart, table, slide rule or the like to obtain the corresponding body fat percentage of the person who has performed the measurement on his/her self.

Figure 5:
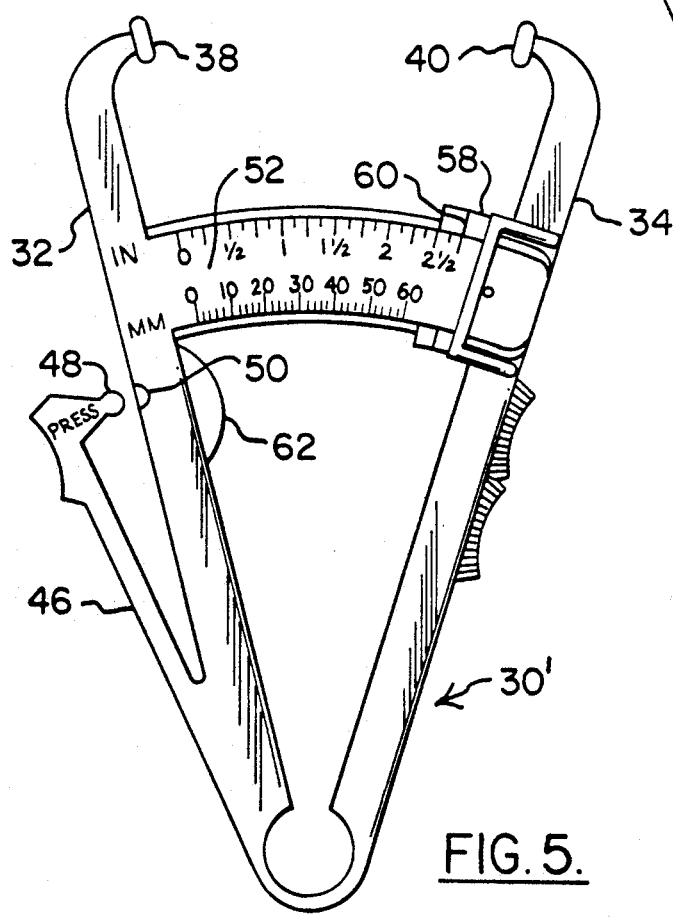
FIG. 5 is a front view of a second preferred possible embodiment of the present invention.

A second possible preferred embodiment is illustrated in FIG. 5. Skinfold caliper 30' is identical to skinfold caliper 30 illustrated in FIGS. 2-4 with the addition of an electronic sensor 66. Sensor 66 senses when clamping surfaces 38, 40 are at the desired pressure level by measuring the strain in arm 32 or by other well known sensing mechanisms. Sensor 66 emits an audible signal when the predetermined pressure level is reached so the person doing the measurement knows that the appropriate pressure has been achieved. The gauged thickness is measured as discussed above.

The present invention is thus able to provide an inexpensive skinfold caliper for accurate self-measurement of body fat percentage of a person without the need for assistance from other people. The above description is for explanatory purposes and is not meant to limit the scope of the claimed inventive concept. Other embodiments and modifications are considered to be within the range of the claimed invention.

I claim:

1. A skinfold caliper for an individual to accurately measure their own body fat, said skinfold caliper comprising:

a first contact surface pivotable about a pivot point;

a second contact surface opposing said first contact surface and pivotable about said pivot point; said first contact surface and said second contact surface operatively connected for clamping against a skinfold to gauge the thickness of the subcutaneous layer of fat of the skinfold;

means on said caliper for measuring said gauged thickness of the subcutaneous layer of fat;

means on said caliper for indicating a predetermined pressure level between said first contact surface and said second contact surface during said measurement, said indicating means including means for directly indicating said predetermined pressure level to the individual being measured regardless of the position of said skinfold caliper; and means on said caliper for retaining said measurement after the skinfold is unclamped.

2. The skinfold caliper of claim 1 wherein said means for indicating a predetermined pressure level includes a cantilevered arm affixed to said caliper;

a first engaging means formed on said cantilevered arm;

a second engaging means formed on said cantilevered arm adapted to receive said first engaging means; and means formed on said first engaging means and said second engaging means preventing said second engaging means from receiving said first engaging means until said predetermined pressure level is exerted.

3. The skinfold caliper of claim 2 wherein said first engaging means include a circular portion extending from said cantilevered arm;

said second engaging means include a concave portion adapted to received said circular portion; and said means for preventing said second engaging means from receiving said first engaging means until said predetermined pressure level is exerted includes a resilient neck portion on said concave portion having a width slightly less than the largest diameter of said circular portion.

4. The skinfold caliper of claim 1 wherein said gauging means include a measuring scale affixed to one of said contact surfaces;

indicator means slidably mounted on said scale to slide relative to said scale; and said retaining means include a third surface affixed to said contact surface engaging said indicator means as said first contact surface and said second contact surface move toward each other and releasing said indicator means as said first contact surface and said second contact surface move away from each other.

5. A skinfold caliper for an individual to accurately measure their own body fat, said skinfold caliper comprising:

a first contact surface;

a second contact surface operatively connected to said first contact surface for gauging the thickness of the subcutaneous layer of fat of a skinfold;

means for measuring the gauged thickness between said first contact surface and said second contact surface; and means for indicating a predetermined pressure force between said first contact surface and said second contact surface, said pressure force indicating means including means for directly indicating said predetermined pressure level to the individual being measured regardless of the position of said skinfold caliper.

6. The skinfold caliper of claim 5 wherein said means for directly indicating said predetermined pressure level includes means for tactually indicating when the pressure force between said first contact surface and said second contact surface is at said predetermined pressure.

7. The skinfold caliper of claim 5 wherein said means for directly indicating said predetermined pressure level includes means for audibly emitting a signal when the pressure force between said first contact surface and said second contact surface is at said predetermined pressure.

8. The skinfold caliper of claim 7 wherein said means for directly indicating said predetermined pressure level further includes means for tactually indicating when the pressure force between said first contact surface and said second contact surface is at said predetermined pressure.

9. The skinfold caliper of claim 5 wherein said means for measuring said gauged thickness includes:
    means for indicating the measurement of said gauged thickness; and
    means for retaining said measurement after the thickness has been measured.

10. The skinfold caliper of claim 5 wherein said means for measuring said gauged thickness includes:
    a measuring scale affixed adjacent one of said first and second contact surfaces;
    a contact member formed adjacent the other of said first and second contact surfaces; and
    indicator means mounted on said measuring scale to slide on said measuring scale from engagement with said contact member as the skinfold is being measured.

11. The skinfold caliper of claim 8 wherein said sliding indicator means disengages from said contact member after the pressure between said first contact surface and said second contact surface is released.

12. A skinfold caliper for an individual to accurately measure their own body fat, said skinfold caliper comprising:
    a first contact surface;
    a second contact surface operatively connected to said first contact surface for gauging the thickness of the subcutaneous layer of fat of a skinfold;
    means for indicating a predetermined pressure force between said first contact surface and said second contact surface, said pressure force indicating means including means for directly indicating said predetermined pressure level to the individual being measured regardless of the position of said skinfold caliper;

means for measuring the gauged thickness between said first contact surface and said second contact surface; and
    means for retaining the measurement of the gauged thickness after the pressure between said first contact surface and said second contact surface is released.

13. The skinfold caliper of claim 12 wherein said means for directly indicating said predetermined pressure level includes means for tactually indicating when the pressure force between said first contact surface and said second contact surface is at said predetermined pressure.

14. The skinfold caliper of claim 12 wherein said means for directly indicating said predetermined pressure level includes means for audibly emitting a signal when the pressure force between said first contact surface and said second contact surface is at said predetermined pressure.

15. The skinfold caliper of claim 12 wherein said means for measuring the gauged thickness includes a measuring scale affixed adjacent one of said first contact surface and said second contact surface;
    a contact member affixed adjacent the other of said first contact surface and said second contact surface; and
    a sliding indicator mounted on said measuring scale to slide relative thereto under engagement with said contact member as said first contact surface and said second contact surface gauge the skinfold and to remain in place relative to said measuring scale as the pressure between said first contact surface and said second contact member is released.

16. A method for an individual to accurately measure their own body fat percentage by using a caliper having opposing contact surfaces operatively connected to gauge the thickness of the subcutaneous layer of fat of a skinfold, a measuring scale and means for indicating a predetermined pressure force between said first contact surface and said second contact surface directly to the individual regardless of the position of said skinfold caliper, said method comprising the steps of:
    (a) pulling a subcutaneous layer of fat away from the muscle tissue of an individual;
    (b) grasping the layer of fat between said opposing contact surfaces;
    (c) applying pressure between said opposing contact surfaces on the layer of fat until the predetermined pressure force is directly indicated to the individual; and
    (d) measuring the gauged thickness of the layer of fat at the predetermined pressure force level.

17. The method of claim 16 wherein said measuring scale includes a sliding indicator engagable by a contact member adjacent one of said opposing contact surfaces and said step (d) further includes:
    releasing the pressure between said opposing contact surfaces;
    measuring the gauged thickness of the layer of fat at the predetermined pressure force level by visually inspecting the location of said sliding indicator which remains in place after the pressure force between said opposing contact surfaces is released.

* * * * *

UNITED STATES PATENT AND TRADEMARK OFFICE
CERTIFICATE OF CORRECTION

PATENT NO. : 5,156,161            Page 1 of 3
DATED : October 20, 1992
INVENTOR(S) : John A. Lollar It is certified that error appears in the above identified patent and that said Letters Patent is hereby corrected as shown below:

In the drawing, Sheet 1, FIG. 2, delete the reference numeral "44" and substitute --42--.

In the drawing, Sheet 1, FIG. 2, the reference numeral 44 should be applied to the concave surface on the upper portion of cantilever arm 46.

In the drawing, Sheet 1, FIG. 2, the reference numeral 62 should be applied to the raised bracket element attached to the upper portion of arm 34.

In the drawing, Sheet 1, FIG. 2, the reference numeral 64 should be applied to the line at the left edge of the raised bracket element attached to the upper portion of arm 34.

In the drawing, Sheet 1, FIG. 3, delete the reference numeral "44" and substitute --42--.

In the drawing, Sheet 1, FIG. 3, the reference numeral 44 should be applied to the concave surface on the upper portion of cantilever arm 46.

In the drawing, Sheet 1, FIG. 3, the reference numeral 62 should be applied to the raised bracket element attached to the upper portion of arm 34.

In the drawing, Sheet 1, FIG. 3, the reference numeral 64 should be applied to the line at the left edge of the raised bracket element attached to the upper portion of arm 34.

UNITED STATES PATENT AND TRADEMARK OFFICE
CERTIFICATE OF CORRECTION

PATENT NO. : 5,156,161

DATED : October 20, 1992

INVENTOR(S) : John A. Lollar

It is certified that error appears in the above-identified patent and that said Letters Patent is hereby corrected as shown below:

In the drawing, Sheet 2, FIG. 4, the reference numeral 62 should be applied to the raised bracket element attached to the upper portion of arm 34.

In the drawing, Sheet 2, FIG. 4, the reference numeral 64 should be applied to the line at the left edge of the raised bracket element attached to the upper portion of arm 34.

In the drawing, Sheet 2, FIG. 5, delete the reference numeral "62" and substitute --66--.

In the drawing, Sheet 2, FIG. 5, the reference numeral 62 should be applied to the raised bracket element attached to the upper portion of arm 34.

In the drawing, Sheet 2, FIG. 5, the reference numeral 64 should be applied to the line at the left edge of the raised bracket element attached to the upper portion of arm 34.

Column 1, line 39, change "Other" to
--other--; line 40, change "procedure measurement" to --measurement procedure--.

Column 2, line 22, change "skin fold"
to --skinfold--.

Column 4, line 40, delete "the"; line
53, change "38" to --48--; line 54, change "38" to --48--.

UNITED STATES PATENT AND TRADEMARK OFFICE
CERTIFICATE OF CORRECTION

PATENT NO. : 5,156,161

DATED : October 20, 1992

INVENTOR(S) : John A. Lollar

It is certified that error appears in the above-indentified patent and that said Letters Patent is hereby corrected as shown below:

Column 5, line 6, change "arms" to
--clamping surfaces--; line 12, delete "o"; line 19, change "52" to --58--.

Col. 7, claim 11, line 1, delete "8" and substitute --10--

Signed and Sealed this

First Day of March, 1994

Attest:

BRUCE LEHMAN

Attesting Officer

Commissioner of Patents and Trademarks